(12) United States Patent
Gupta et al.

(10) Patent No.: US 12,052,640 B2
(45) Date of Patent: Jul. 30, 2024

(54) SYSTEMS AND METHODS FOR CROWDSOURCING REAL-TIME MOBILE CROWD SENSING APPLICATIONS

(71) Applicants: Sandeep Gupta, Tempe, AZ (US); Ayan Banerjee, Tempe, AZ (US); Madhurima Pore, Tempe, AZ (US); Vinaya Chakati, Tempe, AZ (US)

(72) Inventors: Sandeep Gupta, Tempe, AZ (US); Ayan Banerjee, Tempe, AZ (US); Madhurima Pore, Tempe, AZ (US); Vinaya Chakati, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 14 days.

(21) Appl. No.: 17/814,445

(22) Filed: Jul. 22, 2022

(65) Prior Publication Data

US 2022/0369082 A1 Nov. 17, 2022

Related U.S. Application Data

(62) Division of application No. 16/902,036, filed on Jun. 15, 2020, now Pat. No. 11,405,759.

(Continued)

(51) Int. Cl.
| | |
|---|---|
| *H04W 4/38* | (2018.01) |
| *G06N 7/01* | (2023.01) |
| *G06N 20/00* | (2019.01) |
| *G16H 50/80* | (2018.01) |
| *H04L 67/10* | (2022.01) |
| *H04L 67/5683* | (2022.01) |
| *H04W 4/029* | (2018.01) |
| *H04W 4/20* | (2018.01) |
| *H04W 76/10* | (2018.01) |
| *H04W 84/20* | (2009.01) |

(52) U.S. Cl.
CPC ............... *H04W 4/38* (2018.02); *G06N 7/01* (2023.01); *G06N 20/00* (2019.01); *G16H 50/80* (2018.01); *H04L 67/10* (2013.01); *H04L 67/5683* (2022.05); *H04W 4/029* (2018.02); *H04W 4/20* (2013.01); *H04W 76/10* (2018.02); *H04W 84/20* (2013.01)

(58) Field of Classification Search
CPC ......... H04W 4/38; H04W 4/029; G16H 50/80
USPC ...................................... 455/414.1
See application file for complete search history.

(56) References Cited

U.S. PATENT DOCUMENTS

| | | | |
|---|---|---|---|
| 9,619,213 | B2 | 4/2017 | Gupta |
| 9,626,521 | B2 | 4/2017 | Gupta |

(Continued)

FOREIGN PATENT DOCUMENTS

WO WO-2015139119 A1 * 9/2015 ............. G06F 17/30

OTHER PUBLICATIONS

Reddy, et al., 2010. Recruitment framework for participatory sensing data collections. In Proceedings of the International Conference on Pervasive Computing. Springer, 138-155.

(Continued)

*Primary Examiner* — Chuck Huynh
(74) *Attorney, Agent, or Firm* — POLSINELLI PC

(57) ABSTRACT

Various embodiments of systems and methods for mobile crowd sensing applications are disclosed herein.

7 Claims, 10 Drawing Sheets
(7 of 10 Drawing Sheet(s) Filed in Color)

Related U.S. Application Data

(60) Provisional application No. 62/872,881, filed on Jul. 11, 2019.

(56) References Cited

U.S. PATENT DOCUMENTS

| | | | |
|---|---|---|---|
| 9,642,543 | B2 | 5/2017 | Banerjee |
| 9,706,963 | B2 | 7/2017 | Gupta |
| 10,575,788 | B2 | 3/2020 | Gupta |
| 10,671,735 | B2 | 6/2020 | Gupta |
| 10,796,246 | B2 | 10/2020 | Gupta |
| 2013/0317377 | A1 | 11/2013 | Gupta |
| 2015/0170296 | A1 | 6/2015 | Kautz |
| 2017/0215034 | A1 | 7/2017 | Blowers |
| 2019/0188587 | A1 | 6/2019 | Gupta |
| 2019/0354087 | A1 | 11/2019 | Gupta |
| 2020/0108203 | A1 | 4/2020 | Lamrani |
| 2020/0244347 | A1 | 7/2020 | Banerjee |
| 2020/0379575 | A1 | 12/2020 | Banerjee |

OTHER PUBLICATIONS

Sadeghi, et al., 2016. SafeDrive: An autonomous driver safety application in aware cities. In Proceedings of the IEEE Pervasive Computing and Communications Workshops (PerCom'16). 1-6. DOI:https://doi.org/10.1109/PERCOMW.2016.7457095.

Santos, et al., 2018. Fog computing: Enabling the management and orchestration of smart city applications in 5G networks. Entropy 20, 1 (2018).

Sapienza, et al., 2016. Solving critical events through mobile edge computing: An approach for smart cities. In Proceedings of the IEEE International Conference on Smart Computing (SmartComp'16). 1-5.

Saremi, et al., 2016. Experiences with GreenGPS—Fuel-efficient navigation using participatory sensing. IEEE Trans. Mobile Comput. 15, 3 (2016), 672-689.

Satyanarayanan, 2010. Mobile computing: The next decade. In Proceedings of the 1st ACM Workshop on Mobile Cloud Computing and Services: Social Networks and Beyond. ACM, 5.

Sherchan, et al., 2012. Using on-the-move mining for mobile crowd-sensing. In Proceedings of the 13th International Conference on Mobile Data Management (MDM'12). IEEE, 115-124.

Shi, et al., 2017. Real-time target tracking through mobile crowd-sensing. In Proceedings of the Conference on Web Information Systems Engineering (WISE'17), Athman Bouguettaya, Yunjun Gao, Andrey Klimenko, Lu Chen, Xiangliang Zhang, Fedor Dzerzhinskiy, Weijia Jia, Stanislav V. Klimenko, and Qing Li (Eds.). Springer International Publishing, Cham, 3-18.

Simoens, et al., 2013. Scalable crowd-sourcing of video from mobile devices. In Proceedings of the 11th Annual International Conference on ACM International Conference on Mobile Systems, Applications, and Services (MobiSys'13). ACM, 139-152.

Song, et al., 2017. Smart collaborative caching for information-centric IoT in fog computing. In Proceedings of the Sensors Conference.

Sun, et al., 2011. RescueMe: Location-based secure and dependable VANETs for disaster rescue. IEEE J. Select. Areas Commun. 29, 3 (2011), 659-669.

Toledano, et al., 2013. CoCam: A collaborative content sharing framework based on opportunistic P2P networking. In Proceedings of the IEEE Consumer Communications & Networking Conference (CCNC'13). IEEE, 158-163.

Tran, et al., 2017. Collaborative mobile edge computing in 5G networks: New paradigms, scenarios, and challenges. IEEE Common. Mag. 55, 4 (2017), 54-61.

Vanrompay, et al., 2007. Predicting network connectivity for context-aware pervasive systems with localized network availability. In Proceedings of the European Conference on Computer Systems Workshop on the Internet of Things (WoSSIoT EuroSys'07).

Wang, et al., 2017a. Dynamic service placement for mobile micro-clouds with predicted future costs. IEEE Trans. Parallel Distrib. Syst. 28, 4 (Apr. 2017), 1002-1016.

Wang, et al., 2017b.SPACE-TA: Cost-effective task allocation exploiting intradata and interdata correlations in sparse crowd-sensing. ACM Trans. Intell. Syst. Technol. 9, 2, Article 20 (Oct. 2017). DOI:https://doi.org/10.1145/3131671.

Wu, et al., 2016. SmartPhoto: A resource-aware crowdsourcing approach for image sensing with smartphones. IEEE Trans. Mobile Comput. 15, 5 (2016), 1249-1263.

Xiang, et al., 2017. Counter-strike: Accurate and robust identification of low-level radiation sources with crowd-sensing networks. Person. Ubiq. Comput. 21, 1 (Feb. 2017), 75-84.

Zhang, et al., 2017. Sense-aid: A framework for enabling network as a service for participatory sensing. In Proceedings of the International Middleware Conference. ACM.

Ageitgey. 2017. Face Recognition. Retrieved from https://github.com/ageitgey/face_recognition.

Alvear, et al., 2018. Crowd-sensing in smart cities: Overview, platforms, and environment sensing issues. Sensors 18, 2 (2018).

Banerjee, et al., 2015. Analysis of smart mobile applications for health care under dynamic context changes. IEEE Trans. Mobile Comput. 14, 5 (2015), 904-919.

Bao, et al., 2010. Movi: Mobile phone-based video highlights via collaborative sensing. In Proceedings of the 8th International Conference on Mobile Systems, Applications, and Services. ACM, 357-370.

Baresi, et al., 2016. A3Droid: A framework for developing distributed crowd-sensing. In Proceedings of the IEEE International Conference on Pervasive Computing and Communication Workshops (PerCom'16). 1-6.

Bobek, et al., 2017. Uncertain context data management in dynamic mobile environments. Future Gen. Comput. Syst. 66 (2017), 110-124. DOI:https://doi.org/10.1016/j.future.2016.06.007.

Bradai, et al., 2016. Re-OPSEC: Real-time opportunistic scheduler framework for energy awaremobile crowd-sensing. In Proceedings of the 24th International Conference on Software, Telecommunications and Computer Networks (SoftCOM'16). 1-5.

Brouwers, et al., 2012. Pogo, a middleware for mobile phone sensing. In Proceedings of the 13th International Middleware Conference. Springer-Verlag New York, Inc., 21-40.

Capponi, et al., 2017. A cost-effective distributed framework for data collection in cloud-based mobile crowd-sensing architectures. IEEE Trans. Sustain. Comput. 2, 1 (2017), 3-16.

Capra, et al., 2003. Carisma: Context-aware reflctive middleware system for mobile applications. IEEE Trans. Softw. Eng. 29, 10 (2003), 929-945.

Cardone, et al., 2013. Fostering participaction in smart cities: A geo-social crowd-sensing platform. IEEE Commun. Mag. 51, 6 (2013), 112-119.

Chan, et al., 2003. MobiPADS: A reflctive middleware for context-aware mobile computing. IEEE Trans. Softw. Eng. 29, 12 (2003), 1072-1085.

Chen, et al., 2016. Toward real-time and cooperative mobile visual sensing and sharing. In Proceedings of the 35th Annual IEEE International Conference on Computer Communications (INFOCOM'16). 1-9.

Chen, et al., 2018. A mobility management using follow-me cloud-cloudlet in fog-computing-based RANs for smart cities. In Proceedings of the Sensors Conference.

Chon, et al., 2012. CRAWDAD dataset yonsei/lifemap (v. Jan. 3, 2012). Retrieved from https://crawdad.org/yonsei/lifemap/20120103. DOI:https://doi.org/10.15783/C7RW26.

Cortellazzi, et al., 2016. Crowd-sensing and proximity services for impaired mobility. In Proceedings of the IEEE Symposium on Computers and Communication (ISCC'16). 44-49.

da Rosa, et al., 2016. ORACON: An adaptive model for context prediction. Expert Syst. Appl. 45, Supplement C (2016), 56-70. DOI:https://doi.org/10.1016/j.eswa.2015.09.016.

Dastjerdi, et al., 2016. Fog computing: Helping the internet of things realize its potential. Computer 49, 8 (Aug. 2016), 112-116. DOI:https://doi.org/10.1109/MC.2016.245.

(56) References Cited

OTHER PUBLICATIONS

De Rolt, et al., 2016. COLLEGA middleware for the management of participatory mobile health communities. In Proceedings of the IEEE Symposium on Computers and Communication (ISCC'16). IEEE, 999-1005.

Fernando, et al., 2012. Honeybee: A programming framework for mobile crowd computing. In Proceedings of the Annual International Conference on Mobile and Ubiquitous Systems: Computing, Networking and Services (MobiQuitous'12).

Fiandrino, et al., 2017. Sociability-driven framework for data acquisition in mobile crowdsmart cities. IEEE Trans. Sustain. Comput. 2, 4 (Oct. 2017), 345-358. sensing over fog computing platforms for smart cities.

Gambs, et al., 2012. Next place prediction using mobility Markov chains. In Proceedings of the 1st Workshop on Measurement, Privacy, and Mobility. ACM, 3.

Goh, et al., 2012. Online map-matching based on hidden Markov model for real-time traff sensing applications. In Proceedings of the 15th International IEEE Conference on Intelligent Transportation Systems. 776-781.

Guo, et al., 2015. Mobile crowd-sensing and computing: The review of an emerging human-powered sensing paradigm. ACM Comput. Surv. 48, 1, Article 7 (Aug. 2015). DOI:https://doi.org/10.1145/2794400.

Habibzadeh, et al., 2017. Large-scale distributed dedicated- and non-dedicated smart city sensing systems. IEEE Sensors J. 17, 23 (Dec. 2017), 7649-7658. DOI:https://doi.org/10.1109/JSEN.2017.2725638.

Han, et al., 2016. Taming the uncertainty: Budget limited robust crowd-sensing through online learning. IEEE/ACM Trans. Netw. 24, 3 (Jun. 2016), 1462-1475. DOI:https://doi.org/10.1109/TNET.2015.2418191.

Hardawar. Driving app Waze builds its own Siri for hands-free voice control. 2012.

Hassani, et al., 2015. Context-aware recruitment scheme for opportunistic mobile crowd-sensing. Proceedings of the IEEE 21st International Conference on parallel and Distributed Systems (ICPADS'15). 266-273.

Higashino, et al., 2017. Edge computing and IoT-based researchfor building safe smart cities resistant to disasters. In Proceedings of the IEEE 37th International Conference on Distributed Computer Systems (ICDCS'17). 1729-1737.

Hou, et al., 2018. Green survivable collaborative edge computing in smart cities. IEEE Trans. Industrial Info. 14, 4 (2018), 1594-1605.

Hu, et al., 2015. SmartRoad: Smartphone-based crowdsensing for traff regulator detection and identification ACM Trans. Sens. Netw. 11, 4, Article 55 (Jul. 2015).

Hull, et al., 2006. CarTel: A distributed mobile sensor computing system. In Proceedings of the ACM Conference on Embedded Networked Sensor Systems (SenSys'06). ACM, 125-138.

Jayaraman, et al., 2013. Efficie opportunistic sensing using mobile collaborative platform mosden. In Proceedings of the International Conference on Collaborative Computing: Networking, Applications and Worksharing (Collaboratecom'13). IEEE, 77-86.

Jayaraman, et al., 2015. Scalable energy-efficient distributed data analytics for crowd-sensing applications in mobile environments. IEEE Trans. Comput. Soc. Syst. 2, 3 (2015), 109-123.

Karaliopoulos, et al., 2016. First learn then earn: Optimizing mobile crowd-sensing campaigns through data-driven user profiling In Proceedings of the 17th ACM International Symposium on Mobile Ad Hoc Networking and Computing (MobiHoc'16). ACM, 271-280.

Khan, et al., 2016. Moitree: A middleware for cloud-assisted mobile distributed apps. In Proceedings of the 4th IEEE International Conference on Mobile Cloud Computing, Services, and Engineering (MobileCloud'16). IEEE, 21-30.

Kostakos, et al., 2016. Modelling smartphone usage: A Markov statetransition model. In Proceedings of the International Conference on Pervasive and Ubiquitous Computing (UbiComp'16). 486-497.

Lee, et al., 2012. MobiCon: Mobile context monitoring platform: Incorporating context-awareness to smartphone-centric personal sensor networks. In Proceedings of the 9th Annual IEEE Communications Society Conference on Sensor, Mesh and Ad Hoc Communications and Networks (SECON'12). IEEE, 109-111.

Lee, et al., 2013. User mobility-aware decision making for mobile computation offloadin In Proceedings ofthe IEEE 1st International Conference on Cyber-Physical Systems, Networks, and Applications (CPSNA'13). IEEE, 116-119.

Liu, et al., 2017. Energy-aware participant selection for smartphone-enabled mobile crowd-sensing. IEEE Syst. J. 11, 3 (Sep. 2017), 1435-1446. DOI:https://doi.org/10.1109/JSYST.2015.2430362.

Longo, et al., 2017. Crowd-sourced data collection for urban monitoring via mobile sensors. ACM Trans. Internet Technol. 18, 1, Article 5 (Oct. 2017).

Lopez, et al., 2015. Edge-centric computing: Vision and challenges. SIGCOMM Comput. Common. Rev. 45, 5 (Sep. 2015), 37-42. DOI:https://doi.org/10.1145/2831347.2831354.

Lv, et al., 2017. Big data-driven hidden Markov model-based individual mobility prediction at points of interest. IEEE Trans. Vehicular Technol. 66, 6 (2017), 5204-5216.

Meurisch, et al., 2013. Noisemap: Discussing scalability inparticipatory sensing. In Proceedings of the 1st International Workshop on Sensing and Big Data Mining (SENSEMINE'13). Article 6, 6 pages.

Miluzzo, 2007. CenceMe: Injecting sensing presence into social networking applications. In Proceedings of the 2nd European Conference on Smart Sensing and Context. 1-28.

Mokryn, et al., 2012. Help me: Opportunistic smart rescue application and system. In Proceedings of the 11th Annual Mediterranean Ad Hoc Networking Workshop (MedHocNet'12). IEEE, 98-105.

Oskooyee, et al., 2015. Neuro movie theatre: A real-time internet-of-people-based mobile application. In Proceedings of the 16th International Workshop on Mobile Computing Systems and Applications.

Panichpapiboon, et al., 2017. Traff density estimation: A mobile sensing approach. IEEE Common. Mag. 55, 12 (Dec. 2017), 126-131. DOI:https://doi.org/10.1109/MCOM.2017.1700693.

Pore, et al., 2015. Enabling real-time collaborative brain-mobile interactive applications on volunteer mobile devices. In Proceedings of the 2nd International Workshop on Hot Topics in Wireless. ACM, 46-50.

Ra, et al., 2012. Medusa: A programming framework for crowd-sensing applications. In Proceedings of the 10th International Conference on Mobile Systems, Applications, and Services (MobiSys'12). 337-350.

* cited by examiner

SYSTEMS AND METHODS FOR CROWDSOURCING REAL-TIME MOBILE CROWD SENSING APPLICATIONS

CROSS REFERENCE TO RELATED APPLICATIONS

This is a divisional application that claims benefit to U.S. non-provisional application Ser. No. 16/902,036 filed on Jun. 15, 2020 that claims benefit to U.S. provisional application Ser. No. 62/872,881 filed on Jul. 11, 2019, which are herein incorporated by reference in their entirety.

FIELD

The present disclosure generally relates to mobile crowd sensing applications.

BACKGROUND

Mobile crowd sensing (MCS) allows sensor data information to be crowd-sourced from mobile devices in a large group. Mobile device sensors can collect vast quantities and types of data, which can prove valuable in public safety and quality of life applications. For instance, accelerometer and GPS data from mobile devices can be used to identify potholes, road debris, and other problem areas in traffic. GPS and camera data from mobile devices in close proximity can also be used to quickly locate and identify a perpetrator during an attack.

MCS enables development of context aware applications by mining relevant information from a large set of devices selected in an ad hoc manner. However, MCS could be potentially used for much more demanding applications such as real-time perpetrator tracking by online mining of images from nearby mobile users. Since MCS applications assume an unreliable underlying computational platform, most typical sample sizes for recruited devices are guided by concerns such as fault tolerance and reliability of information. As the real-time requirements get stricter, coupled with increasing complexity of data mining approaches, the communication and computation overheads can impose a very tight constraint on the sample size of devices needed for realizing real-time operation. This results in trade-off in acquiring context relevant data and resource usage incurred while the real-time operation requirements get updated dynamically. Such effects have not been properly studied and optimized to enable real-time MCS applications such as perpetrator tracking It is with these observations in mind, among others, that various aspects of the present disclosure were conceived and developed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Corresponding reference characters indicate corresponding elements among the view of the drawings. The headings used in the figures do not limit the scope of the claims.

DETAILED DESCRIPTION

Figure 1:
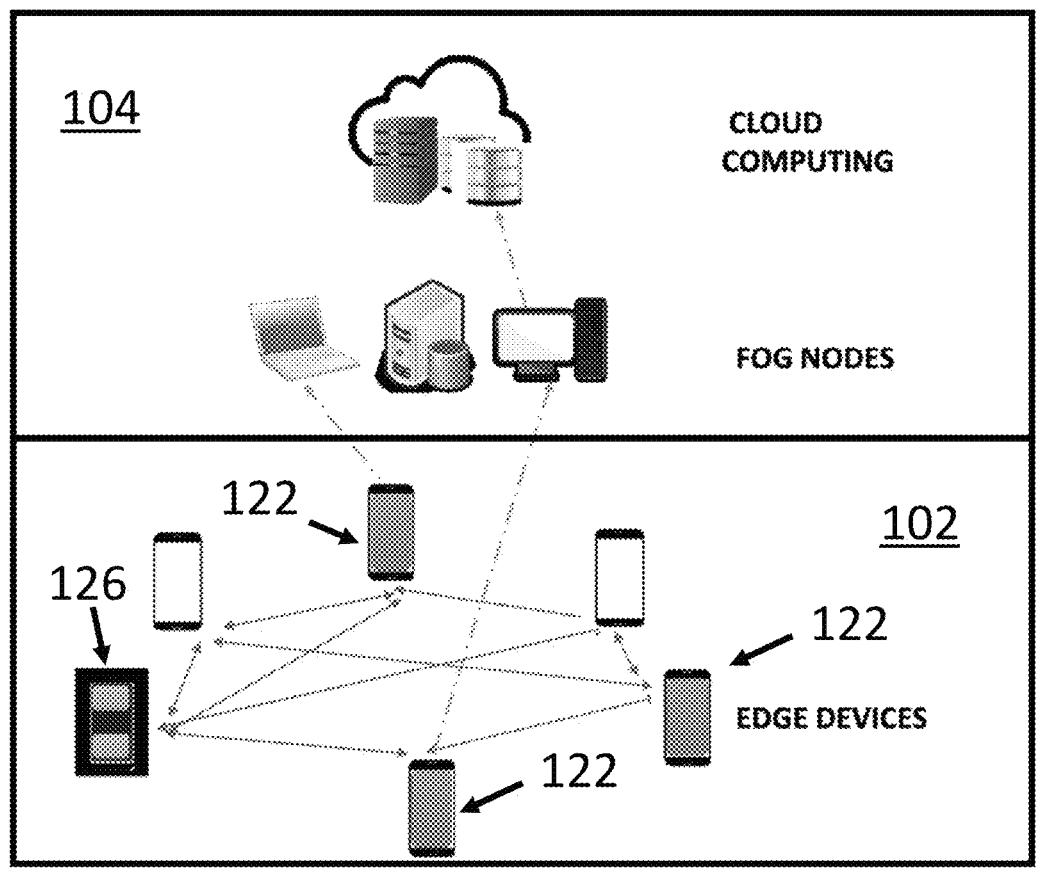
FIG. 1 is a diagram showing an overview of the present system for sourcing MCS application data.

Various embodiments of a system and associated method for tracking using a mobile crowd sensing (MCS) for such complex processing in real-time are disclosed herein. The present system is embodied as a combination of an API, middleware, and an optimization engine running on one or more servers in communication with one or more volunteer mobile devices. The present system includes a method for recruiting volunteer mobile devices for execution of computation and communication heavy MCS applications in an edge environment. Referring to the drawings, embodiments of the present system are illustrated and generally indicated as 100 in FIGS. 1-10.

Referring to the drawings, FIG. 1 shows an overall network of the system 100 including one or more fog devices 104 in communication with one or more volunteer mobile devices 102. The one or more fog devices 104 can be embodied as one or several computing devices, and in some embodiments the one or fog devices 104 may be virtual or cloud-based servers. The one or more volunteer devices 102 may include one or more selected devices 122, which are selected based on their device capabilities and whether or not the selected devices 122 meet various requirements, herein referred to as "context requirements", via an optimization method 300 (FIG. 3). In addition, one or more leader devices 126 may be included among the one or more selected devices 122 to facilitate publishing of an MCS request to other volunteer devices 102 and in some embodiments, establish communication with the one or more fog devices 104. Once the one or more selected devices 122 are established, the one or more selected devices 122 can donate resources for sensing, processing, and execution of analytical tasks for the MCS application. In some embodiments, each task forms part of a framework 200 (FIG. 2) which is split between the one or more fog devices 104 and the one or more volunteer devices 102.

Figure 2:
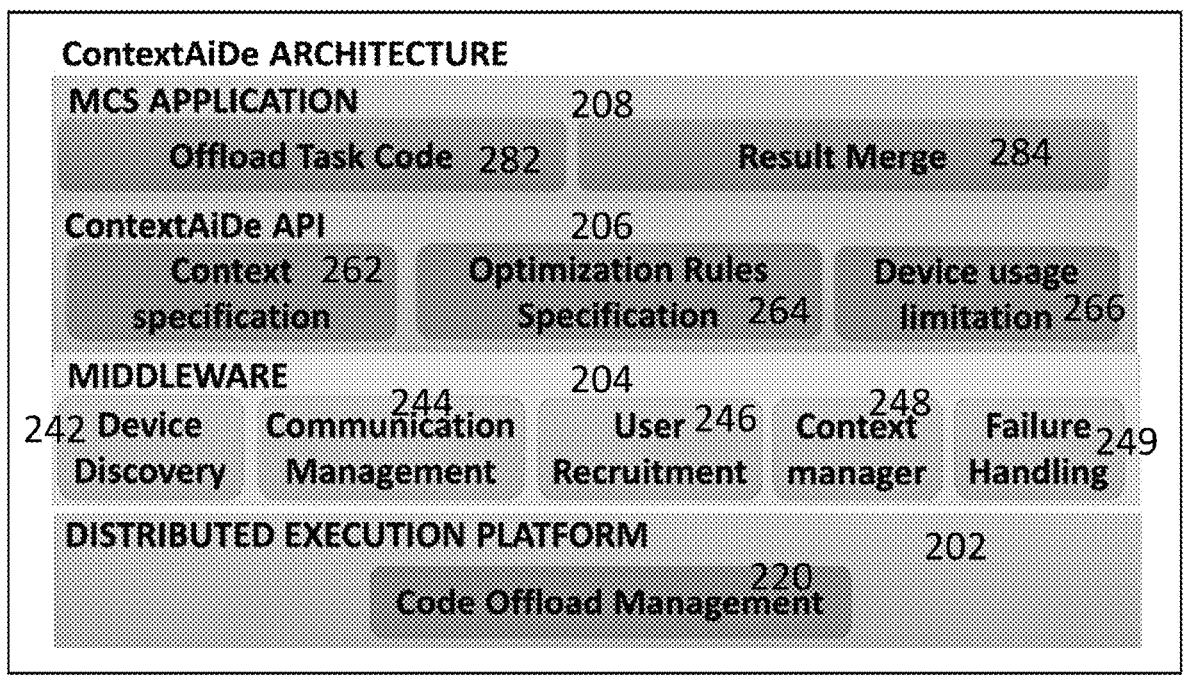
FIG. 2 is a diagram showing an the overall software architecture of the present system for execution of the system of FIG. 1.
Figure 3:
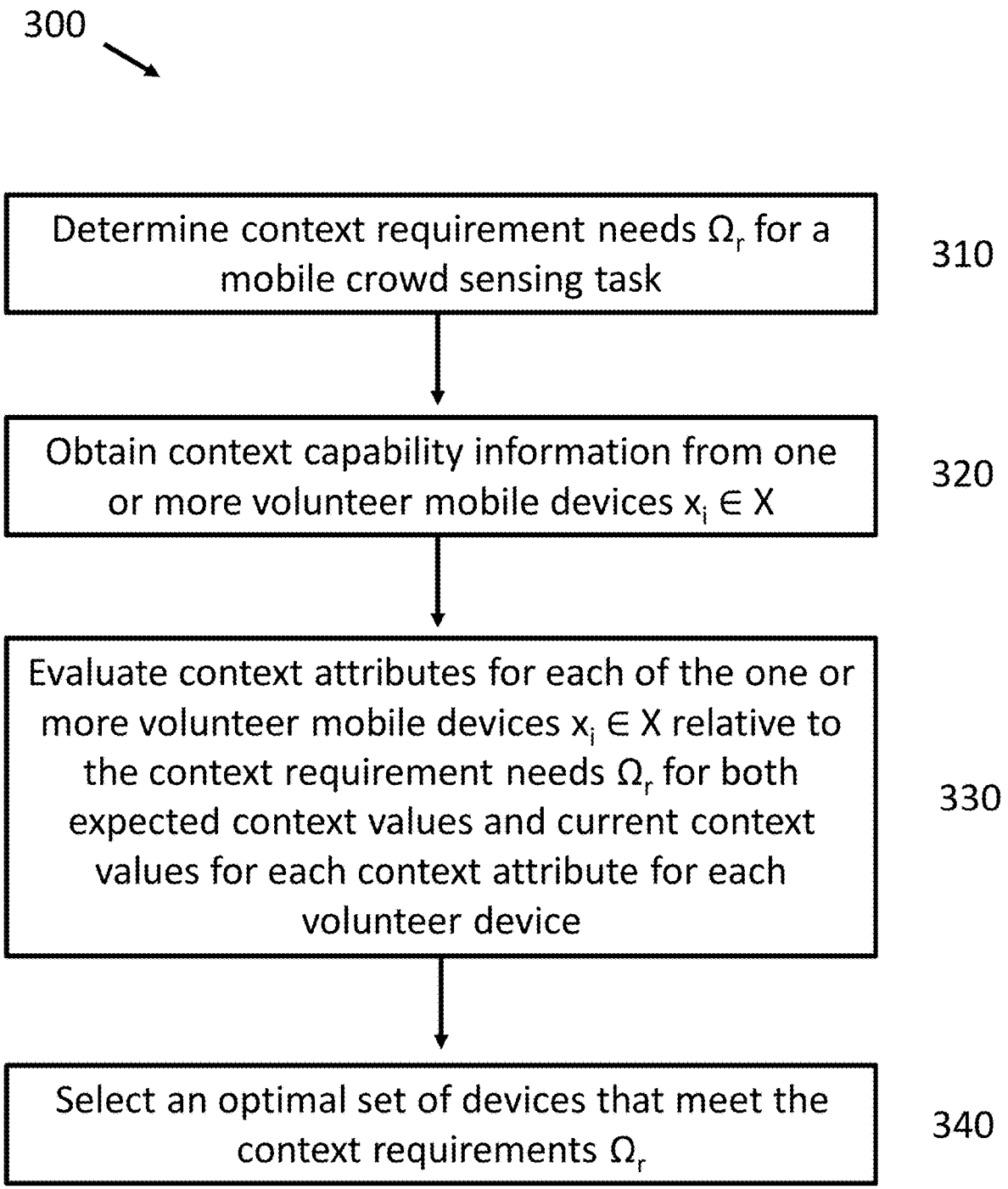
FIG. 3 is a flowchart showing an overall method for selecting volunteer mobile devices for execution of the system of FIG. 1.

Referring to FIG. 2, the framework 200 as embodied by the present system 100 uses a notion of two types of contexts, exact (hard constraints) which must be completely satisfied, and preferred (soft constraints) which may be satisfied to a certain degree. By adjusting the preferred contexts, the present system 100 can optimize the operational overheads to enable real-time operation. The framework 200 of the system 100 includes an application programming interface (API) 206 and middleware 204, that collectively facilitate: a) specification of MCS application context requirements and task distribution between fog devices 104 and volunteer devices 102, b) continuous context monitoring on the volunteer devices 102, c) distributed execution of application components, and d) stochastic optimization of operational overheads and application computational and communication footprint while meeting the real-time context requirements, and volunteer device 102 resource constraints for execution of a reliable MCS application 208 through dynamic volunteer selection.

The present system 100 provides the platform 200 for optimizing user recruitment, distributed execution overhead, and computational and communication needs while meeting the time constraints. It assumes two types of context requirements for an MCS application 208: a) exact contexts (these are hard constraints that have to be met by a participating volunteer device 102); and b) preferred contexts (these are soft constraints typically on application contexts and device resources). These constraints are associated with a degree of context matching (i.e. to participate, the preferred context value has to be within a given degree of deviation from a reference value). The preferred contexts allow the present system 100 to derive a set of volunteer devices 102 (also known as "edge" devices) that enable adaptation to changing context requirements and continue real-time execution of MCS application 208 by optimizing computation, communication requirements and operational overheads. Referring to FIG. 2, the framework 200 of the present system 100 has four components:

a) A distributed execution platform 202, where pre-decided parts of the application 208 can be executed on selected volunteer devices 102 and other parts can be offloaded to the fog devices 104.

b) Middleware 204 provides the following functionalities:
Device discovery 242: Communicates the application request to available volunteer devices 102.

User recruitment 246: Refines and recruits the devices 102 selected by optimizing the preferred context requirements of the MCS application 208 under the device resource constraints. A recruitment decision is then revised for dynamically updated context requirements and changing availability of contexts on devices executing the task.

Continuous context monitoring 248 and failure handling 249: Monitors contexts of volunteer devices 102 at the desired interval and maintains a history. During execution of MCS tasks, continuous context monitoring 248 and failure handling 249 re-evaluate context availability and initiates recruitment process if required.

Communication Management 244: Communication management 244 is responsible for establishing and maintaining the communication link between different volunteer devices 102 and the fog devices 104 through various mechanisms including, but not limited to WiFi, WiFi direct, Bluetooth and 4G.

c) The API 206 is a programming interface through which a developer can specify MCS application context requirements both high level and fine-grained, device resource limitations, and parameters of the optimization processes (used in user recruitment), context prediction and monitoring, and real-time MCS application performance.

d) MCS application 208 allows a developer to write the MCS application code for a volunteer device 102 running Android OS and identify portions of the code that can be offloaded.

The present system 100 has four principal novelties:
a) The present system 100 classifies into two types of context requirements—high level (exact) and softer constraints (preferred). The preferred context allows for variations in the information quality, which results in a better opportunity for optimized operation.

b) The present system 100 also allows stochastic optimization of computation, communication, and operational overheads, to select the best set of selected devices 122 that facilitate accurate and real-time execution of the MCS application 208.

c) Proactively learning usage data of the volunteer devices 102; the present system 100 performs stochastic optimization to recruit volunteer devices 102 that achieve desired accuracy reducing the failures in uncertain user environments.

d) Monitoring the contexts closely, the present system 100 revisits user recruitment to continue execution in presence of dynamic context changes in user devices 102.

System Architecture

The overview of the framework 200 of the system 100 that can support execution of MCS application 208 on an edge environment is disclosed herein. Any volunteer device 102 that has the MCS application 208 installed may connect to other nearby volunteer devices 102, subscribe to a common publish-subscribe channel facilitated by the API 206, and participate in sensing and execution of the MCS application 208. A participating device 102 can be configured either as a leader device 126 or standard volunteer device 102.

FIG. 1 shows that initially, a volunteer device 102 that first initiates the MCS task in the edge environment is configured as a leader 126 and some of the volunteer devices 102 are recruited. A leader 126 publishes an MCS request and volunteer devices 102 that are ready to donate sensing or processing resources are configured as volunteer devices 102. Initially, all the volunteer devices 102 communicate through a common channel facilitated by the API 206 and a one-one communication link is established with selected volunteer devices 102. These devices 102 are selected for sensing, processing the data and execution of analytical task respectively. The leader device 126 requests contextual information from the volunteer devices 102 and recruits the optimized set of selected devices 122 that match the contextual requirements of the application. Sensed data is either processed locally or sent to the other volunteer devices 102 that are selected as processing nodes. Servers 104 may be utilized for complex processing before results are sent to the leader device 126. In the framework 200 of the present system 100, it is considered that the MCS application 208 has a set of contextual requirements $\Omega$.

Context Optimization Formulation: The framework 200 of the present system 100 architecture defines a way to compare context on different volunteer devices 102 and further adopts a two-stage stochastic optimization. In this section, definitions of context are stated and formulation is given for two-stage context optimization used in the framework 200 of the present system 100.

Figure 4:
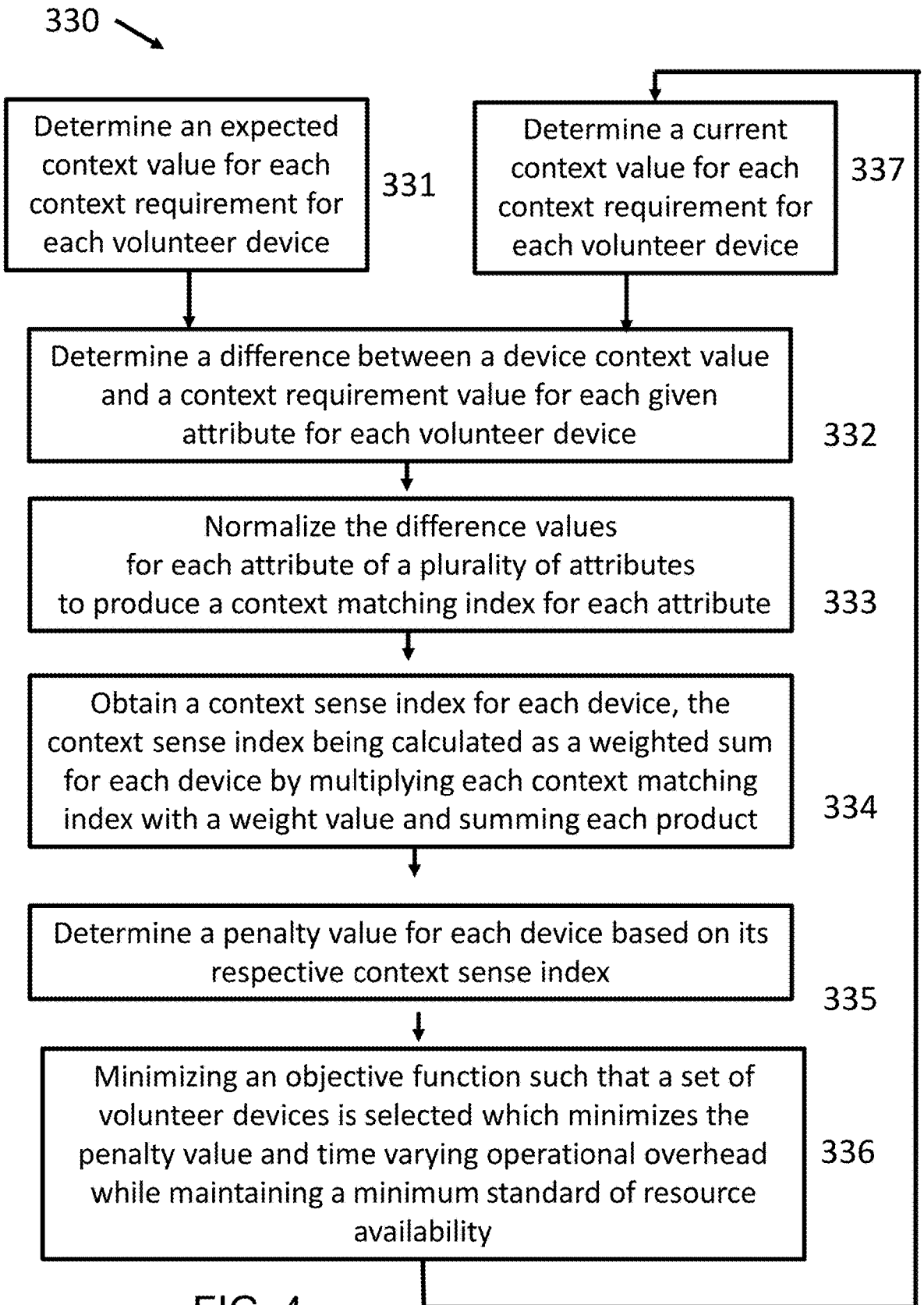
FIG. 4 is a flowchart showing a method for evaluating context attributes for each volunteer device as executed by the system of FIG. 1.

Referring to FIGS. 3 and 4, a method 300 is included for selecting an optimal set of devices 122 that meet context requirements is disclosed herein. In block 310, context requirement needs for the MCS application 208 are first determined. Context capability information is obtained from one or more volunteer devices 102, as shown in block 320. Further, block 330 shows evaluating the context attributes for each of the volunteer devices 102 relative to the context requirements for both expected context values and current context values for each volunteer device 102. Step 330 is a two-step optimization process, elaborated on below and in FIG. 4. Referring back to FIG. 3, the final optimized set of volunteer devices 102 that meet the context requirements are selected.

Referring to FIG. 4, the two-step optimization process 330 is outlined. The first step is to select devices 122 based on expected context values. The second step verifies the devices 122 by re-evaluating the selection with actual empirical context values. In block 331, expected context values in the form of key-value pairs $\{\psi, C\}$ are determined for each context requirement for each volunteer device 102. In block 332, a difference is determined between a context value for each attribute for a volunteer device 102 and a context requirement. In block 333, the difference values are normalized to produce a context matching index for each attribute. In block 334, a content sense index is determined for each device 102, the context sense index being representative of a weighted sum of context matching indices (as determined in block 334) to essentially quantify how the device 102 is qualified to meet the context requirements. In block 335, a penalty value is determined for each volunteer device 102 based on the context sense index (i.e. the greater the sum of normalized differences between context values and context requirements, the less qualified the volunteer device 102 is). Block 336 shows minimizing an objective function to select devices 122 that meet the context requirements. This objective function serves to reduce a penalty amount and operational overhead while maintaining a minimum standard of resource availability.

The second step repeats this process outlined in blocks 332-336, with the exception being that instead of determining an expected context value, current context values based on real-time measurement are determined and used to obtain a final list of selected devices 122, as shown in block 337.

Definition 1: Context: Context is a key-value pair $\{\psi, C\}$ where $\psi$ is an attribute of the mobile volunteer device 102, and C is a value taken by the attribute $\psi$ on the volunteer device 102. This corresponds to block 320 of FIG. 3. A context can either be an exact context or a preferred context. Exact and preferred context is denoted by $\{\psi^x, C^x\}$ and respectively. Collection of multiple contexts associated with the volunteer device 102 is referred to as a Context Set and is represented as $\Omega$. Some of the contexts in $\Omega$ maybe have regular usage patterns ($\Omega'$) and while others may be related to environmental conditions and are thus not related to the user. Examples of contexts that have regular usage patterns are battery level, location, and network connectivity. Contexts such as camera resolution is an example of context without any usage patterns since it is a property of the volunteer device. An MCS application 208 can have K context requirements and the context requirement set $\Omega_r$ is given by $\{\{\psi_1, C_1\}, \{\psi_2, C_2\} \ldots \{\psi_K, C^K\}\}$. Some of these requirements can be hard for exact contexts or soft for preferred contexts. Important contributions of the present system 100 such as user recruitment are designed based on context.

To evaluate if a volunteer device 102 meets the context requirements of an application 208, a distance metric is defined between the context available on a volunteer device and the context requirements. This step corresponds with block 332 of FIG. 4.

Definition 2: Context Distance: For a given attribute $\psi$, context distance is the difference between the context values Ca on the volunteer device 102 and requirement $C_r$ and is represented using a function $\delta(., .)$ that takes the context values as input and outputs a real number. Context distance for the exact and preferred contexts are given as follows:
1. $\delta(C_d^x, C_r^x)=0$ for exact context, and
2. $0 \leq \delta(C_d^p, C_r^p) \leq \epsilon$ for preferred context, where $\epsilon$ is an application specific parameter decided for the accurate operation of the MCS application 208.

Even within the preferred context, some attributes can have a large acceptable distance such as battery power, or some might have smaller acceptable distances such as location. In an optimization setting, it is always beneficial to normalize the distances so as to avoid giving preference to one preferred context based on its acceptable distance. Hence, a context matching index is defined, corresponding to block 333 in FIG. 4.

Definition 3: Context Matching Index: Context Matching Index I is defined as the ratio of the context distance of a given preferred context to the acceptable deviation $\epsilon$:

$$I = \frac{\delta(C_d^P, C_r^P)}{\epsilon}.$$

Preferred contexts may be independent of each other. In order to optimize user recruitment to maximize the matching of all preferred contexts, it is best to utilize an objective function that is a weighted sum of the context matching indexes of the preferred contexts. Optimization objectives such as minimizing the maximum context matching index do not have significant advantages over weighted sum as there is no correlation between preferred contexts, but such objectives unnecessarily complicate the problem. Hence, the context sense index is define, corresponding to block 334 of FIG. 4.

Definition 4: Context Sense Index: Context Sense Index for a mobile volunteer device 102 is defined as the sum of weighted context matching index for each preferred context $C_d^P$ in $\Omega_d$:

$$Y_d = \sum_{k=1}^{K} w_k, I_k,$$

where $w_k$ is the weight associated with the context $\delta(\psi_k^P, C_k^P)$ and is used to set priorities for the preferred context. Sum of the weights for a given context set is 1. Consider an MCS application 208 that is composed of multiple sensing tasks, each with a set of context requirements. Context requirements are denoted by set Or (Refer to Definition 1). Mobile devices 102 that are available for performing crowd sensing tasks are represented as shown below, as set X where, N=|X|. A device $x_i$ 102 from set X may or may not be selected by the present system based on the required context availability, where $$X = \{x_1, x_2, x_3 \ldots, x_N\} | x_i \in \{0,1\}.$$

Of these, N' volunteer devices 102 match the exact contextual requirements of the application (N'≤N). This set is denoted by $S_H$. The present system selects an optimized set of S selected devices 122 from $S_H$ with the objective of minimizing the context sensing index. Based on the application requirements such as the minimum number devices $N_S$ there can be constraints (such as lower bounds) on the cardinality of the set S.

Dynamic User Recruitment through Stochastic Optimization: As the context on mobile volunteer devices 102 is associated with some uncertainty, Stage 1 uses expected values of context to choose an optimal set of selected devices 122. Once the real-time usage values become available, the selection decision is revisited in Stage 2. Given a request for $N_S$ volunteer devices 102 that meet the context requirements $\Omega_R$, the user recruitment approach first selects a set $X_H$ where N'>S and each volunteer device 102 matches the exact context, i.e. $\delta(C_{x_i}^x, C_r^x)=0$, $\forall x_i \in X_H$ As discussed above, the framework 200 of the present system 100 then aims to select an optimized set of selected devices 122 from the set $X_H$ using two stage optimization:

Stage 1: As discussed above, the first stage determines the optimized set of selected devices 122 with minimal context deviation by using stochastic models of the historical trends for resource and operational overheads to determine an expected context value, corresponding to block 331 in FIG. 4. The optimization stage of the framework 200 computes the expected values of the contexts and are dependent on the usage history and mobility of the user. In some embodiments, for other context attributes in the context set $\Omega$, the system 100 obtains the current values on the volunteer device 102. Expected values and current values of different contexts and the number of volunteer devices 102 required are used in the optimized user recruitment algorithm described above to obtain the optimized set of selected devices 122 for the sensing task. Expected values are computed using several stochastic models discussed above and are used to reduce the failures caused due to a lost context such as mobility, network connectivity and battery level on the volunteer device 102. Here $m_i(\psi_i^P)$ is the stochastic model of the context $\delta(\psi_i^P, C_i^P)$ in terms of the attributes based on the historical usage or mobility data. $E[m_i(\psi_i^P)]$ and $C_i$ (in $P_i$, below) are the expected and current value of context on device i.

$$I_k' = \begin{cases} \frac{\delta(E[m_i(\psi_i^P)], C_r^P)}{\epsilon} & \forall C \subset \Omega', \\ 1 & \forall C \not\subset \Omega'. \end{cases}$$

$$Y_i' = \sum_{k=1}^{K} w_k I_k'.$$

The optimization algorithm assumes that device selection is associated with a penalty of $P_i$ (block 335) given as:

$$P_i = \begin{cases} Y_i' & [\{\delta(E[m_i(\psi_i^P)], C_r^P) \le \epsilon \forall C \subset \Omega'\}, \\ & [\{\delta(C_i^P, C_r^P) \le \epsilon \forall C \not\subset \Omega'\}, \\ \gg 1 & \text{Otherwise.} \end{cases}$$

The objective function for finding the optimized set of volunteer devices 102 (block 336) is formulated as follows:

$$\min \sum_{i=0}^{N'} x_i, P_i,$$

$$x_i \in \{0, 1\},$$

$$x_i \subset X_H$$

$$\text{s.t. } \sum_{i=0}^{N'} x_i \ge S$$

$$\tau_i^s(t) + \tau_i^r(t) < \tau^T$$

$$R_i(t) - R_i^\ominus(t) > R_i^T.$$

where $P_i$ is the penalty associated with the selection of device, S is the number of devices required for assigning the sensing task. $\tau_i^s(t)$ is time taken for data sensing and $\tau_i^r(t)$ is the data transfer time and is the execution time constraint. Both $\tau_i^s(t)$ and $\tau_i^r(t)$ represent the time varying operational overheads. Such overheads also vary for different volunteer devices and stochastic models have to be used in order to estimate such details. The present system 100 uses a data driven approach towards modeling such delays and is application specific. $R_I$ is the current resource availability and $R_i^\ominus$ the amount of resource usage on the volunteer device 102. $R_i^T$ is the limit set on the resource usage by the device owner. $R_i^\ominus$ is obtained from observing the previous usage history of the person. Stochastic models for $R_i^\ominus$ is discussed in further detail.

Stage 2: In this stage, the optimization decision of stage 1 is refined based on the actual context values available on the volunteer devices 102 for all the context attributes in $\Omega$, as shown in block 337. The same objective function as in stage 1 is followed. However, during this stage, validation is attempted to see if the optimized set of stage 1 is a valid optimized set with the current context values on the selected set of devices. If all the volunteer devices 102 in the selected set are within the acceptable context deviation then there will not be any task reassignment as it incurs additional overhead. But if one or more devices of the optimized set of selected devices 122 are no longer in the acceptable context deviation range then the architecture tries to find a new set of selected devices 122 within an objective of minimal context deviation. Selected devices 122 that have been selected for sensing task during the first stage of optimization and still retain the context within an acceptable deviation range. Unlike the stage 1 of optimization where the expected values are used for the context variables in stage 2, the actual context values are used. Context distance is calculated as $\delta(C_i^P, C_r)$. This stage selects a new optimized set of selected devices $S_H'$ 122 from the set $S_H$ using the current values of context for assigning the sensing task. The penalty (block 335) for a device in stage 2 optimization is given by:

$$P_i = \begin{cases} Y_i' & | \{\delta(C_i^P, C_r) \le \epsilon\} \quad \forall C \subset \Omega, \\ \gg 1 & \text{Otherwise.} \end{cases}$$

and the objective function (block 336) is given by $$\min \sum_{i=0}^{N'} x_i, P_i, \quad | x_i \in \{0, 1\},$$

where $x_i$ is volunteer device 102 selected for sensing task and $P_i$ is penalty associated with device i. In addition to context requirements of an application, the mobile volunteer devices 102 have their own device contexts. These are defined in terms of the system variables related to the computation and communication properties of the devices 102, specifically, the mobile device, the cloudlet, and the cloud.

A possible attempt at representing a mobile volunteer device 102 in terms of variables used in the context definition can be as follows:

User defined preferences: The framework 200 of the present system 100 also allows a user to set bounds on device resources that can be used by the offloaded task of the mobile application 208. Such preferences can be strict bounds, e.g., a user might only want to execute the task only if the offload task code does not reduce the device state of charge by more than 2% as suggested in recent studies. Such user preferences are specified by $U_d$, which are values associated with the system variables $\psi_d^x \cup \psi_d^p$ of the mobile volunteer device 102.

User Recruitment: Each volunteer device 102 maintains a history of context values for context set $\Omega'$. If the leader requests a context specific to the MCS application 208, these values are sent to the leader device 126. A subset $S_H$ is selected based on the exact context matching. Further Stage 1 optimization is performed giving a selection of selected devices 122. These selected devices 122 are communicated and offload code is executed on the selected devices 122. During execution if the context on a particular selected device 122 deviates beyond constraints, the leader device 126 is communicated and Stage 2 of the optimization is initiated using the actual values of context.

Usage Models: In this example, three types of usage models are predicted: location, network connectivity, and battery state. These are dependent on user mobility and device usage. The LifeMap dataset is used which collected fine grained mobility data for over two months. It has been observed that these contexts follow a regular pattern. Diverse mathematical approaches such as time series prediction, machine learning techniques are used to develop a model that runs continuously on user devices. The present system 100 can also predict physiological contexts changes if the model and sensor is available. Proactive context prediction can improve the user recruitment thereby improving the performance of MCS applications 208.

TABLE 1

| Network State | Description |
|---|---|
| $v_0$ | WiFi |
| $v_1$ | 3 G |
| $v_2$ | No Connectivity |

| Battery State | Soc range |
|---|---|
| $\beta_0$ | $0 \leq Soc \leq 20$ |
| $\beta_1$ | $20 < Soc \leq 40$ |
| $\beta_2$ | $40 < Soc \leq 60$ |
| $\beta_3$ | $60 < Soc \leq 80$ |
| $\beta_4$ | $80 < Soc \leq 100$ |

Location prediction: A history of location data is used to learn the user location pattern. A transition matrix is used that consists of the recently visited location of the user. In the present system, five recent locations were used which form the transition matrix. GPS location data used from the database updates the transition matrix every 10 minutes updating the probability of transition from the previous location to the current location.

To capture the hourly pattern, a separate transition matrix for each hour of the day is maintained. This matrix updates the location transitions of the same hour every day and thus captures the daily pattern of the user. It also updates the transition matrix for frequently visited set of locations during the hour. Location for next step is estimated using the transition matrix and a current user location.

Network state prediction: Network states shown in Table 1 are used to build a transition model which is updated every 10 minutes. A separate transition matrix is used for each hour of the day. These matrices help to capture diurnal pattern of network transitions. A matrix for a given hour and current network state is used to predict the network state in next window.

Battery state prediction: Different battery states in Table 1 and charging status of the battery are used for prediction. In the present model, a separate transition matrix is used for charging and discharging. Battery data updates the transition matrix at an interval of 10 minutes. Current battery level and the transition matrix that is chosen based on the charging state of the battery is used to predict battery level in the next time step.

Distributed Execution Platform 202: The distributed execution platform 202 is the backbone for managing code offload. Predefined offload sensing and processing tasks are handled by this module. The module performs a task assignment and also merges the results from the volunteer devices 102.

Middleware 204: The middleware 204 of the framework 200 provides functions to find available volunteer devices 102, establish communication links, optimize and select required devices that are common to many MCS applications.

Device Discovery 242 finds all the nearby mobile volunteer devices 102 through a published-subscribe model. Volunteer devices 102 participating in the present system 100 subscribe to a common channel. A volunteer device 102 executes an MCS application 208 by configuring itself as a leader device 126 by publishing a crowd sensing request on the channel. The volunteer devices 102 respond to the request based on the availability of context on the volunteer device 102.

Communication Management 244 is responsible for establishing a connection between the leader 126 and all the selected devices 122 having the required context. Communication management sets up an individual connection between the leader device 126 and each volunteer device 102. On the leader device 126, communication management periodically inspects for lost and new connections.

User Recruitment 246 is responsible for selection of volunteer devices 102 that will execute the MCS task. It uses the context matching and the optimization rules specified in the application design. Initially, exact context matching is performed on the user devices to filter the volunteer devices 102 which do not match. Further two-stage optimization is performed. Stage 1 uses a combination of expected and actual values of the device context. The constraints of optimization are based on user limitations, device resource constraints, and MCS application 208 constraints. It also uses the profiling of MCS task, data usage and communication times. As the execution is in progress context available on the volunteer device 102 may change or there may be a change context requirement. Stage 2 is responsible for obtaining updated device contexts and revising the recruitment decision.

Failure Handling 249 using the predicted context for recruitment is discussed in this section. Dynamic usage and mobility of the mobile user may lead to change or loss of context during execution. This may result in task failures. Change or loss of context is detected by the Context Manager. This module monitors device, user activity and event within an environment to infer the context changes. The present system 100 handles failure through a Reactive-Leader and Reactive-Volunteer approach. In Reactive-Leader approach context change is notified immediately to the leader device 126 and the leader device 126 decides to select another suitable volunteer device 102 for sensing. In Reactive-Volunteer approach, whenever the context of the volunteer device 102 changes, it configures itself as leader device 126 and delegates sensing task to a new set of volunteer devices 102.

API 206: The API 206 of the present system 100 provides programming abstractions that ease the development of MCS application 208. Context definition, context requirement specification, optimization rule specification, device usage limitation are important abstractions provided by the API 206.

Context requirement Specification 262: The API 206 of the present system 100 defines classes that can be used to define contexts and specify context requirements set of the application. The requirement set includes exact and preferred contexts. Exact context requirements take a single definitive value whereas preferred context requirements can accept a range of values.

Optimization Rules Specification 264: This helps in improving user recruitment decision and enriching the crowd sensed data while minimizing context deviation and resource usage. Some of the optimization rules include the number of crowd-sourced devices required for collecting data, real-time constraints of the application execution and the priorities for different context requirements. For example, data has to be sent to the required device within a given time. Optimization also considers context prediction for user recruitment. Context prediction parameters will enable the developer to set the granularity of prediction intervals and prediction windows.

Device Usage Limitations 266: For encouraging participation in crowd sensing the present system enables volunteer device owners to set a threshold on the resource usage. Access to some sensors can also be restricted. Optimization module takes into account these constraints during the user recruitment.

MCS Application 208: The framework 200 integrates the MCS application 208 into the present system 100 using the API 206. MCS application 208 includes the following modules: offload task code 282 and result merge 284.

Offload Task Code 282 encapsulates the logic of sensing or processing task. It is provided by a developer in a form of DEX code which is offloaded to a selected device. This code has a implementation of the method senseData( ) and processData( ) Volunteer device 102 invokes the sense and process methods to execute the task on the volunteer device 102.

Result Merge 284 module combines the results of processing nodes 104 using mergeResult( ) sent through DEX code to construct the output of the MCS application 208. Another mode of communicating results is to upload all the result files to a URL of a fog or cloud server embodied through the fog devices 204.

Implementation

In this section, details of modules in the framework 200 of the present system 100 are presented. An MCS application 208 can be integrated into the framework 200 by using the API 206 for its development, along with its requirements in the form of an android application. For the MCS application 208, context requirements, optimization rules, context prediction parameters, time constraints, and required resources are specified. Code offloading is used for distributing the sensing and processing tasks. All volunteer devices 102 have the present system 100 installed. The device requesting MCS task is configured as a leader device 126. This framework 200 is responsible for volunteer device discovery, context monitoring and optimization, user recruitment, data collection, and data processing. Perpetrator tracking is used as an example application.

Figure 5:
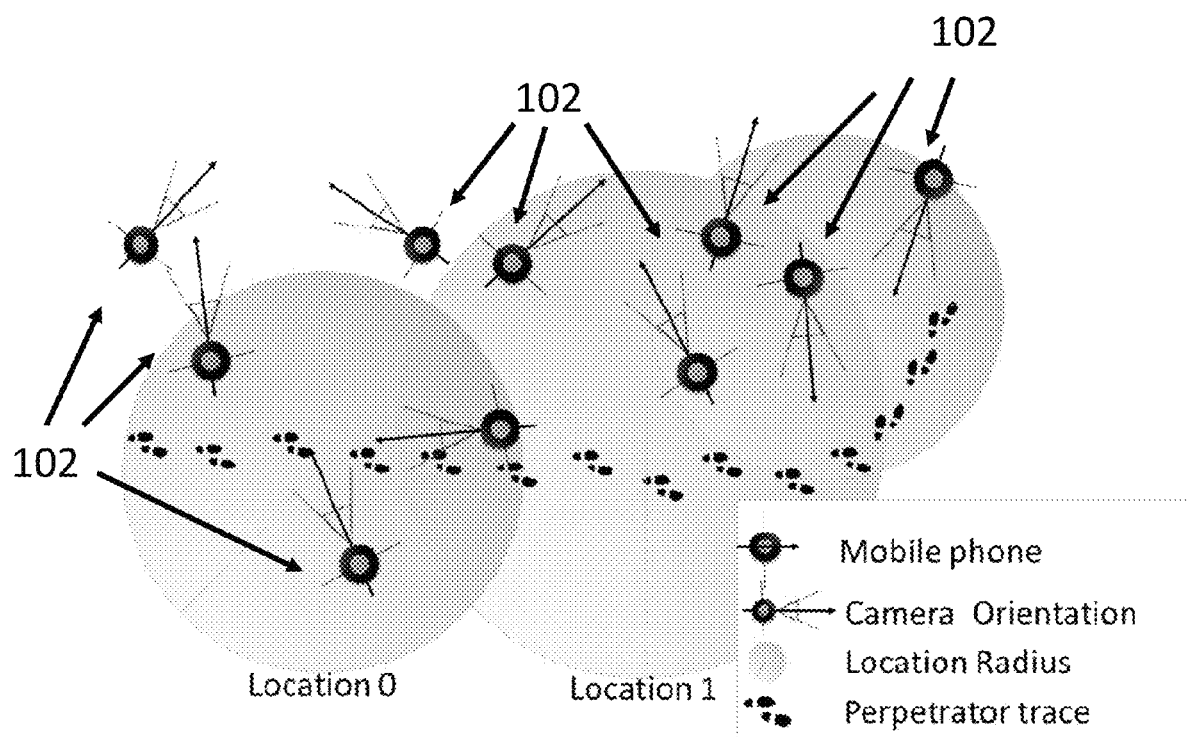
FIG. 5 is an illustration showing a visual representation of the perpetrator-tracking mobile crowd sensing application of FIG. 1.

Perpetrator Tracking Example: This example, shown in FIG. 5, shows the use of the present system 100 to track a perpetrator in real-time is called InvestigatorAssist application. The input to the present system 100 is intelligence about the initial location of an untoward event of interest involving a perpetrator. Input may also include an image or silhouette of the perpetrator. The application then selects volunteer devices 102 in the vicinity of the initial location and obtains device parameters such as the accelerometer, orientation, WiFi availability, battery state and Camera parameters. The accelerometer is used to minimize movement artifacts in the image capture while the orientation controls the angle of image capture. Location radius is a radial distance from given location and it defines the search area of the perpetrator. The goal is to maximally match the above context requirements. Volunteer devices 102 with an orientation favorable to capture image, stationary, and with sufficient resources capture and upload pictures to the cloud. The cloud then uses a silhouette matching algorithm to identify the perpetrator in the images. These results are used to update the location of the perpetrator. The image capture, silhouette matching, and location update occur in a few seconds.

Infectious Disease tracking: In some embodiments, the present system 100 can be employed to map users and regions which are affected by infectious diseases. The present application 100 can collect data from volunteer devices 102 and aggregate the data to develop a connection map (not shown). The connection map is a mesh structure that indicates who has come in close proximity with whom and during a given time frame. Mesh maps can be correlated with symptom data which can be obtained from volunteer devices 102 to inform users about social distancing recommendations or alert them to start monitoring their symptoms more rigorously in case of potential contact with an infected person.

A recommended method to determine whether an individual is an asymptomatic carrier of a virus or infectious disease is to perform a molecular test in a laboratory. Lack of testing equipment for a novel virus, such as SARS-Cov-2, implies that tests are only reserved for symptomatic individuals who meet certain other criterion related to travel, demography, and co-morbidity. Hence, asymptomatic carriers are not tested and tracked optimally. Mobile contact tracing as aided by the present system 100 can be used for all individuals in a given country irrespective of testing, albeit at the behest of significant amount of computation and storage resources. This can lead to indiscriminate quarantine and strict social distancing which can potentially affect critical aspects of society such as the economy. Moreover, in addition to slowing the spread, contact tracing should also aid reopening of economic or non-essential activities. To address such challenges, it is argued that while mobile technology based contact tracing as enabled by the system 100 is useful it must be integrated with a detection mechanism for asymptomatic carriers.

MCS Requirements:

Context Request: Different Context attributes that are important for Investigator Assist app are specified through API 206. In perpetrator tracking, the different attributes are the GPS location, orientation, battery level, availability of WiFi, user activity (stationary, moving), as shown in Table 2. Leader device 126 requests contextual information from the available nearby devices 102 connected to it. Exchange of Contextual information between the volunteer device 102 and leader device 126 is designed using a serialized object. The distance functions for each of these context attributes are also provided. The contextual information is used by the optimization method 300 on leader device 126.

TABLE 2

| Context | Value | Deviation | Type | Details |
|---|---|---|---|---|
| Location | Event Location | 0 | exact | GPS value specify event location |
| Camera | Availability | 0 | exact | Ensures that the camera is available for use by The present system |
| Wifi | Availability | 0 | exact | Ensures connectivity to communicate the MCS data |
| Activity | 1 | 0 | exact | Not moving user reduces noise in camera output |
| Battery | 70% | 30 | preferred | Prefer the devices with higher battery levels |
| Location radius (m) | 0 | 20 | preferred | Defines the search area for locating perpetrator |
| Orientation | 300° | 20° | preferred | Ensures specific direction of viewing as requested by the investigator. |

Optimization Rules: The rules of optimization enable to select the devices that are within a certain radius of the perpetrator. The real-time requirements such as execution time and device usage constraints are specified in the optimization rules. The priority of preferred contexts is set through weights associated with each context.

Volunteer Device limits: Users can set limits on usage of volunteer devices 102 such as battery level, Data usage, and sensors. These limitations are considered in runtime while matching of context on the device and execution of the task.

Middleware 204 Functions: Volunteer device discovery is accomplished through a published-subscribe model. In the present implementation, PubNub Java API is used. All the participating devices subscribe to a common channel. Whenever app request is initiated, the leader device 126 writes IP address to the channel. This message is read by the volunteer devices 102 and they connect to the leader device 126 over a TCP socket connection.

Execution Module: Leader device 126 sends the DEX of the sensing and processing task to the devices selected by the user recruitment algorithm. Volunteer devices 102 start the sensing task by invoking senseData( ) method. Data collected is processed locally invoking processData( ) or it may be sent to the processing/fog/cloud server. In perpetrator tracking example, the sensing task involves taking pictures in a fixed time interval. The processing task on mobile includes detecting images with faces while the fog server task is recognition of the perpetrator.

Optimized User Recruitment Algorithm 300: Referring to FIG. 3, after determining context requirement needs (step 310), the next step 320 in the user recruitment process is to obtain the contextual information of the connected volunteer devices 102. Volunteer devices 102 find the expected values for the user dependent contexts such as the battery (dependent on usage patterns) and the location and WiFi (dependent on user mobility). The expected values are based on a prediction window of 10 minutes as determined by the present usage model. For contexts that are not user dependent such as camera availability, the volunteer device 102 obtains the current value.

A user recruitment step 330 solves the two-stage optimization problem and selects a subset of $S_H$ of cardinality S. The problem in the objective function is an integer linear program. However, the values of $x_i$ can either be 1 or 0. Moreover, the objective function is linear with respect to the set of volunteer devices 102. User recruitment algorithm can first consider the set $S_H$, where each volunteer device 102 in $S_H$ already satisfies the exact contexts. If $S_H$ has less than S volunteer devices 102 then the application run is incomplete.

Otherwise, $S_H$ is sorted on basis of CSI and topmost S devices 122 are selected. This selection decision is communicated to volunteer devices 102.

As the execution progresses, on each volunteer device 102 if the context deviation exceeds beyond limits, stage 2 is initiated. Even though stage 1 optimization decision is based on 10 minute window, in stage 2, optimization is performed with updated actual context values. This ensures continuous availability of required context on the devices that are recruited. In both stages, the resource limitations and real-time constraints are obtained by profiling the tasks, data transfer delays. After stage 2, a final optimal set of selected devices 122 is identified that meet the context requirements (step 340).

Profiling MCS Application Tasks: This section profiles the Sensing, communication and processing time for Investigator Assist app. The cloud VM is set up in Google Cloud with 8vCPUs and 32 GB memory. A fog server was also set up in the Arizona State University network with an Intel i7 Desktop 3.5 GHZ Quad core CPU, 16 GB RAM.

Figure 6:
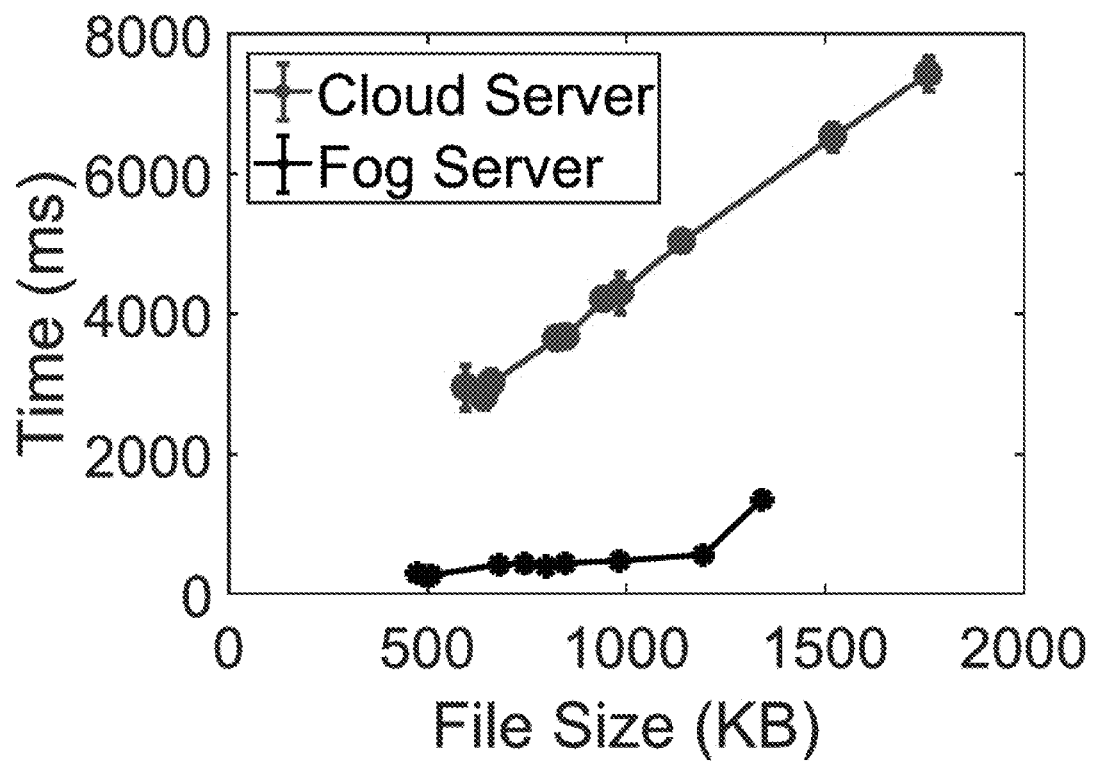
FIG. 6 is a graphical representation of the times a cloud server and a fog server take to transfer a file with respect to file size.
Figure 7:
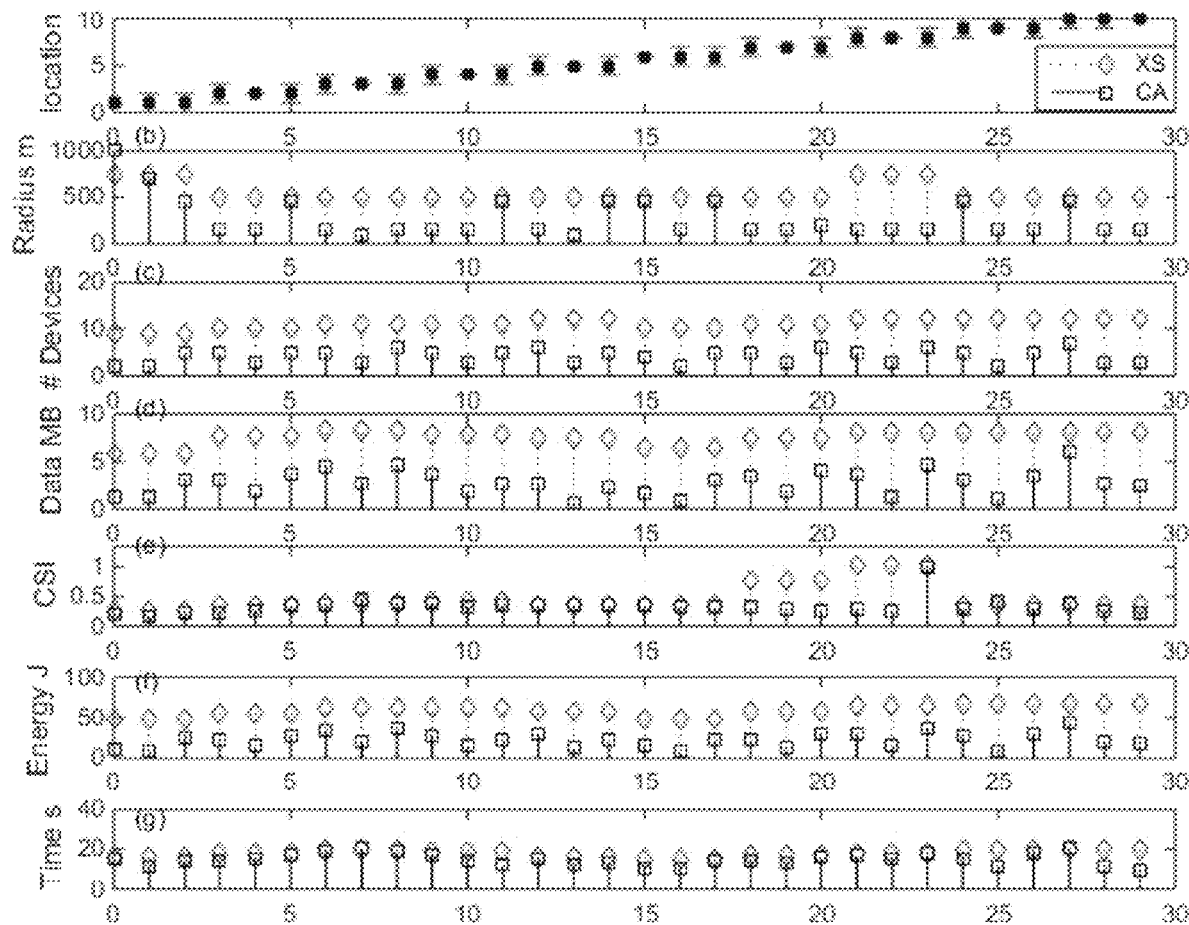
FIG. 7 is a graphical representation of a perpetrator tracking scenario.

Profiling File transfer time: One of the common methods to upload camera images to the server is saving the file on the device before sending it to the server using multipart file upload. FIG. 6 shows the time incurred to send the original camera images to the Cloud and the Fog server. Different file sizes are obtained by using multiple resolution setting of Camera to capture images ranging from 500 KB to 2 MB which are sent using lossless compression. The time between the start of data transfer and receipt of the acknowledgment is file transfer time.

Profiling Data Sensing Time: The time for sensing is noted on the Android device from the receipt of sensing request to the time data is available on the device for transfer. For different file sizes, the sensing time was observed as 2203.9±397 ms.

Profiling Execution time of MCS tasks: Execution of the perpetrator tracking MCS application 208 involves running of face detection application on the mobile device and face recognition application on the Fog/Cloud server. The time for running the MCS task is time between the start of processing the file and availability of results. Average time incurred for varying file sizes is 1161 ms with a standard deviation of 331.69 ms for face detection task while face recognition task requires average 860 ms with a standard deviation of 101.8 ms.

For evaluation run, the time starting from request for image capture to the time when results of face recognition are generated as a combined time for sensing and data transfer time for a single image is estimated. Time incurred using the file saving method is estimated to be 8.6 s for cloud and 4.71 s for Fog server processing.

Evaluation

The framework 200 of the present system 100 is evaluated using an InvestigatorAssist application on an edge environment that includes a small group of volunteer devices 102, local fog server (104), and a cloud server (104). Evaluation run uses two execution environments:
1. It runs on the actual set of volunteer devices 102 which is described in this section;
2. It is a simulated set of volunteer devices 102 that use historical user data of LifeMap data set collected in a free moving environment.

Experimentation setup: For experiment evaluation, 14 volunteer devices 102, one notebook 102, a fog server 104, and a cloud server 104 were used. Specification details of these devices are listed as follows:
(1) 6 One Plus One phones, Qualcomm Snapdragon 2.5 GHz Quad core CPU, 3 GB RAM, 64 GB Storage, Android 5.1.1
(2) 4 Nexus 5 phone, Qualcomm Snapdragon 2.3 GHz Quad core CPU, 2 GB RAM, 32 GB Storage, Android 5.1.1
(3) 2 LG g2 phone, Qualcomm Snapdragon 2.26 GHz Quad core CPU, 2 GB RAM, 16 GB Storage, Android 5.1.1
(4) 1 Nexus 7 tablet, Qualcomm Snapdragon 1.5 GHz CPU, 2 GB RAM, 32 GB Storage, Android 5.1.1
(5) 1 Moto G5 plus phone, Qualcomm Snapdragon 2.0 GHz CPU, 4 GB RAM, 64 GB Storage, Android 7.0
(6) Fog Server: Intel i7 Desktop 3.5 GHZ Quad core CPU, 16 GB RAM
(7) Cloud server in Google Cloud with 8vCPUs and 32 GB memory All the volunteer devices 102 have the app installed. InvestigatorAssist app is distributed on the volunteer devices 102. Sample context definitions are shown in Table 2. One of the volunteer devices 102 as the leader device 126 and initiates sensing task request by publishing its IP address on the published-subscribe channel. Image capture and face detection are sensing and processing tasks that are offloaded and executed on the volunteer devices 102 available in the edge environment. Face recognition task is hosted on the fog and cloud servers 104.

Volunteer Device Tasks: Image capture and face detection are the volunteer device tasks of the InvestigatorAssist App. Image Capture task captures images at the rate specified in the runtime contextual requirements. Face Detection is invoked as soon as the file captured is saved.

Server Tasks: Face recognition is the server task of the InvestigatorAssist App. This task is executed on the Fog or Cloud server to process data from users in the smallest time to make the results available to the leader device 126. While tracking the perpetrator, image data containing faces from the images obtained is sent to the server 104. The server 104 processes these images to identify the perpetrator. The existing Open source python based face recognition library which internally uses deep learning models is used to recognize the perpetrator. Using the model of the perpetrator's face, it can detect if the perpetrator's image was captured by any of the volunteer devices 102.

Perpetrator Tracking Evaluation: The present system 100 is evaluated using Investigator Assist App which tracks a perpetrator, who is running through a series of locations. This evaluation is performed using 14 android volunteer devices 102 available at a given location at a time with varying context values. Initial reference location and search radius are provided at the beginning of the run. At a given location, the present system 100 optimally selects volunteer devices 102 that acquire images from a camera. MCS application 208 components involve two processing components: 1) detecting images that contain faces (runs on a mobile device which captures images.) and 2) recognizing the face in the image sent (runs on the Fog server). Once a perpetrator is detected, this application obtains the next reference location and adjusts the search radius on the basis of the movement of the perpetrator (See FIG. 5). The devices are chosen optimally based on predicted context and available context abbreviated as CA. This is compared to existing strategy (XS) where volunteer devices 102 are selected with optimal context but the search radius is fixed and the next location is the last known location of the perpetrator. FIG. 6 shows 30 minute run of tracking a perpetrator. Performance of the present system 100 vs. XS is shown in Table 3 in a single request which tracks perpetrator through location 1 to the 10.

TABLE 3

| Plot (XS, CA) | Value | Description |
|---|---|---|
| (a) tracked | Location | Location tracked by both methods indicates perpetrator tracked within search area |
| (b) 542, 221 | Radius | Plot indicates search radius (here mean) |
| (c) 86%, 31.7% | Devices | Number of devices (here percentage) |
| (d) 7.5 MB, 2.8 MB | Data | Average data sent by sensing devices to fog server every minute |
| (e) 0.459, 0.335 | CSI | Lower CSI indicates better Contextual data acquired |
| (f) 59.6J, 22.6J | Energy | Average Mobile Energy Consumption every minute |
| (g) 17.9 s, 14.8 s | Time | Average time incurred for processing a request |

Evaluation with Other Recruitment Strategies

This evaluation is designed using real-life mobile volunteer device 102 traces from LifeMap Dataset. Ten requests of Investigator assist app of average duration of 30 minutes are generated to track a person moving in the campus area. An evaluation of user recruitment is presented and compared with the user recruitment of prior research works to analyze for different performance factors like accuracy, energy savings, data transfer, and incomplete requests.

LifeMap Dataset: This dataset has sensor data acquired from 11 people on the campus of Yonsei University. Data from 11 users is obtained during different periods; data from 8 users over the period of one month is used when data from maximum users are available. Data traces of GPS locations are extracted as well as battery level, connectivity, and user activity with a time granularity of 2 minutes.

Strategies for User Recruitment: In this section, different user recruitment approaches are described in detail.
1. Existing Strategy (XS): This user recruitment scheme is similar to Context Aware Task Allocation (CATA) where context optimized selection is performed for each new task request. Next location is given by one of the volunteer devices 102 that recognize the perpetrator while the search radius is fixed.
2. Ideal (I): This recruitment revises the selection decision by performing optimization at fixed time intervals to select optimally context matching volunteer devices 102. In the evaluation presented, the time interval is set for 2 minutes. This recruitment scheme chooses devices with best CSI in every time step to provide optimal user selection.
3. Current Available Context (CA): This approach employs a user recruitment scheme discussed above. Currently available context on the device is used by this approach. Optimization is performed for user recruitment when the required context becomes suddenly unavailable or context request is initiated.
4. Stochastic (CAS): This approach is similar to the CA approach but the context used in device selection is the predicted context of the device. Context is predicted using a stochastic approach.
5. Cloud (CAC): This uses the aforementioned user recruitment strategy, but cloud is used for processing. The present system's user recruitment schemes are designed to adapt to dynamically changing context requirements, e.g. location or search radius may change based on the movement of the perpetrator. New location and search radius are obtained using results of the previous evaluation.

Evaluation using Data Traces: In this section, the present system 100 is evaluated for strategies discussed above. Parameters are as follows:
(1.) CSI: Lower CSI value indicates data acquired matches the required context.
(2.) Data Usage: Sensed data is acquired on the mobile device is data sent to fog/cloud server for processing after local processing except in CAC where data is processed in Cloud. Amount of data transferred by different algorithms is compared.
(3.) Energy: The energy is estimated on basis of data sensing, processing and data transfer that are executed on the mobile device while processing each application request.
(4.) Number of Optimizations: In a given sequence of application requests, the number of optimizations indicate the operational overhead of the algorithm and depends on recruitment algorithm.
(5.) Devices switched: Sum of new devices that were recruited during execution.
(6.) Incomplete requests: Context-aware recruitment of devices causes some of the request to be incomplete. A total number of request that remains incomplete over the sequence of requests.
(7.) Delay: Average time incurred to accomplish MCS task.
(8.) Accuracy: It shows the distance between the actual and the estimated location of the perpetrator.

Figure 8:
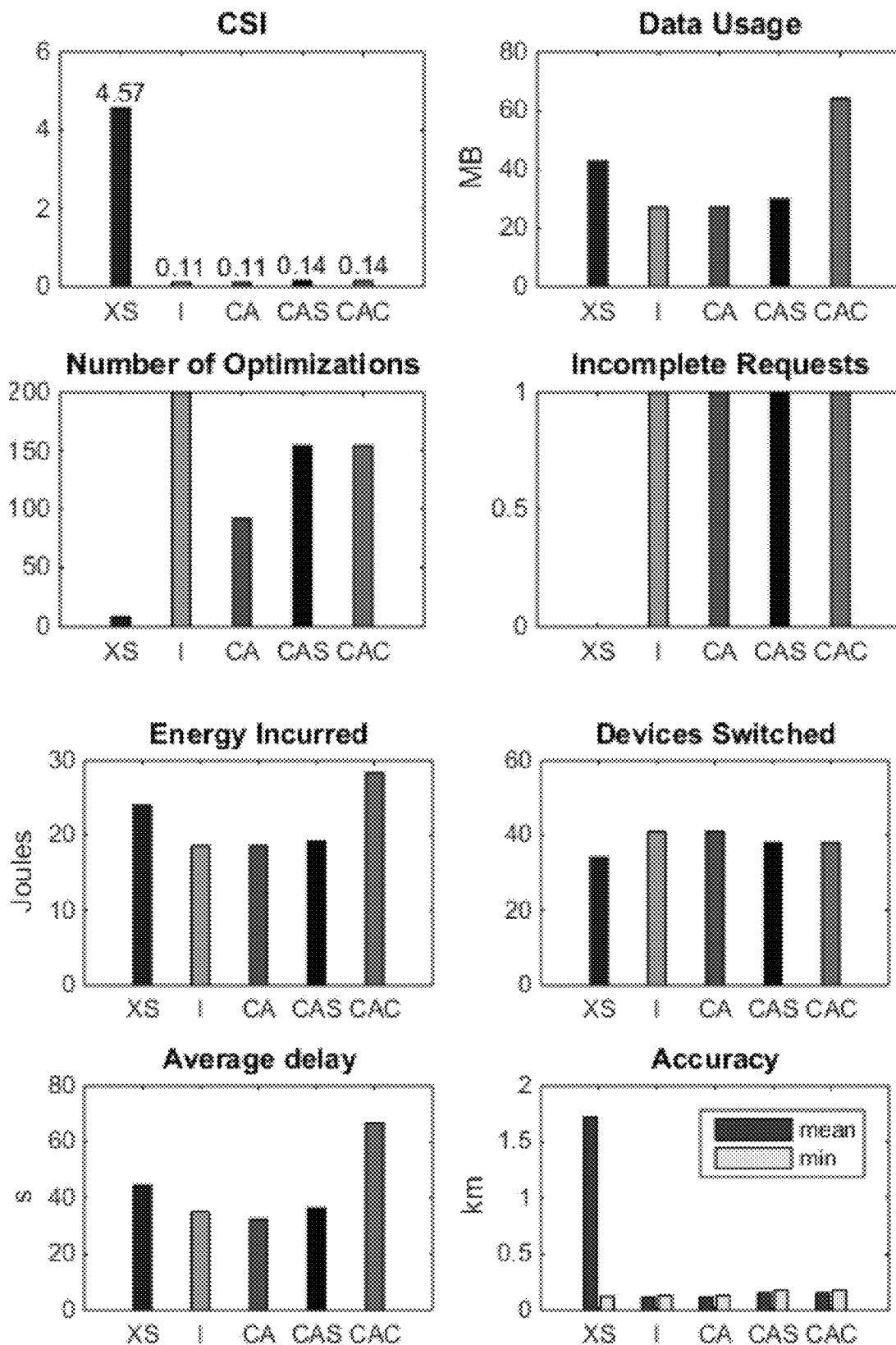
FIG. 8 is a graphical representation of the performance of the present system in comparison with the performance of other MCS systems.
Figure 9:
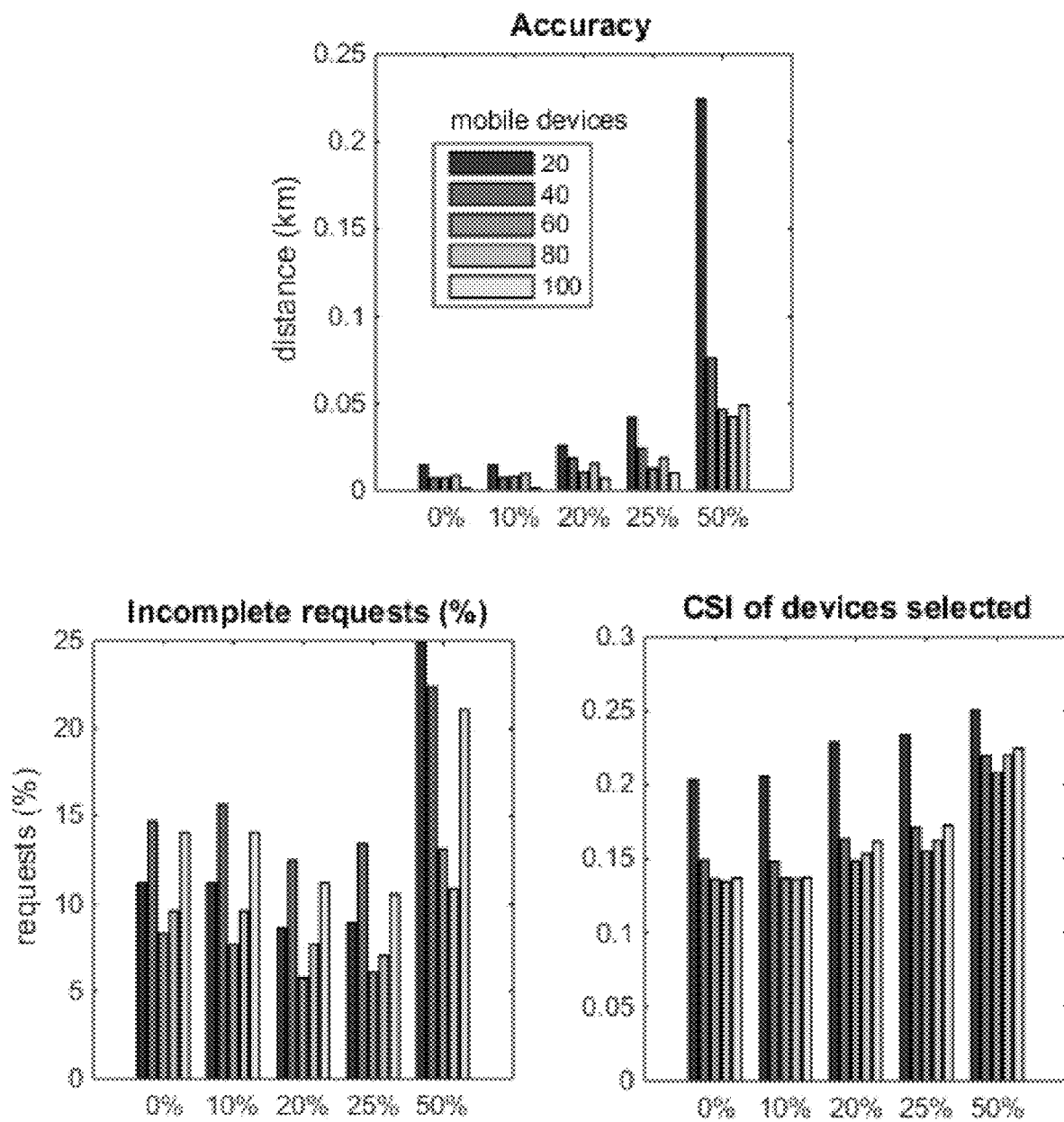
FIG. 9 is a graphical representation of the performance of the present system during variable uncertainty scenarios.

FIG. 8 shows that CA successfully generates context relevant data shown by lower CSI and accuracy plot. CAS using proactive context results in little better energy and delay performance. Data used in CAS is 24.8% lesser and energy is 37.8% lower than existing strategy (XS) for accurately tracking the perpetrator. Time incurred is improved by 43%. This is achieved using CSI optimization indicated by the accuracy plot. Close monitoring of context and proactive decision based on expected context values results in savings of data usage energy consumption and time incurred. However, this comes at the cost of accuracy. Minimum distance achieved in CA, CAS is a little more than XS and I strategy but the mean value of XS is much higher than CA/CAS. Alternatively, using the cloud server in CAC strategy incurs much higher energy (33%) and delay (50%) than CAS. In order to evaluate the performance of CAS strategy, a simulation was set up with varied number of mobile users for executing InvestigatorAssist application. The mobility, WiFi, battery, activity are modeled according to the LifeMap usage data. Performance of CAS is evaluated for variation in uncertainty that is associated with Contextual data. FIG. 9 shows the variation in accuracy, percentage of incomplete request (due to unavailability of context) and average CSI which shows context relevance of data obtained. For lower uncertainty (<20%) accuracy is as desired less than 40 m. Percentage of requests abandoned and CSI of devices selected remain steady for lower uncertainty (<25%). But as uncertainty increases, higher values of CSI are noted for high at the cost of increased incomplete requests and lower accuracy.

Exemplary Computing System

Figure 10:
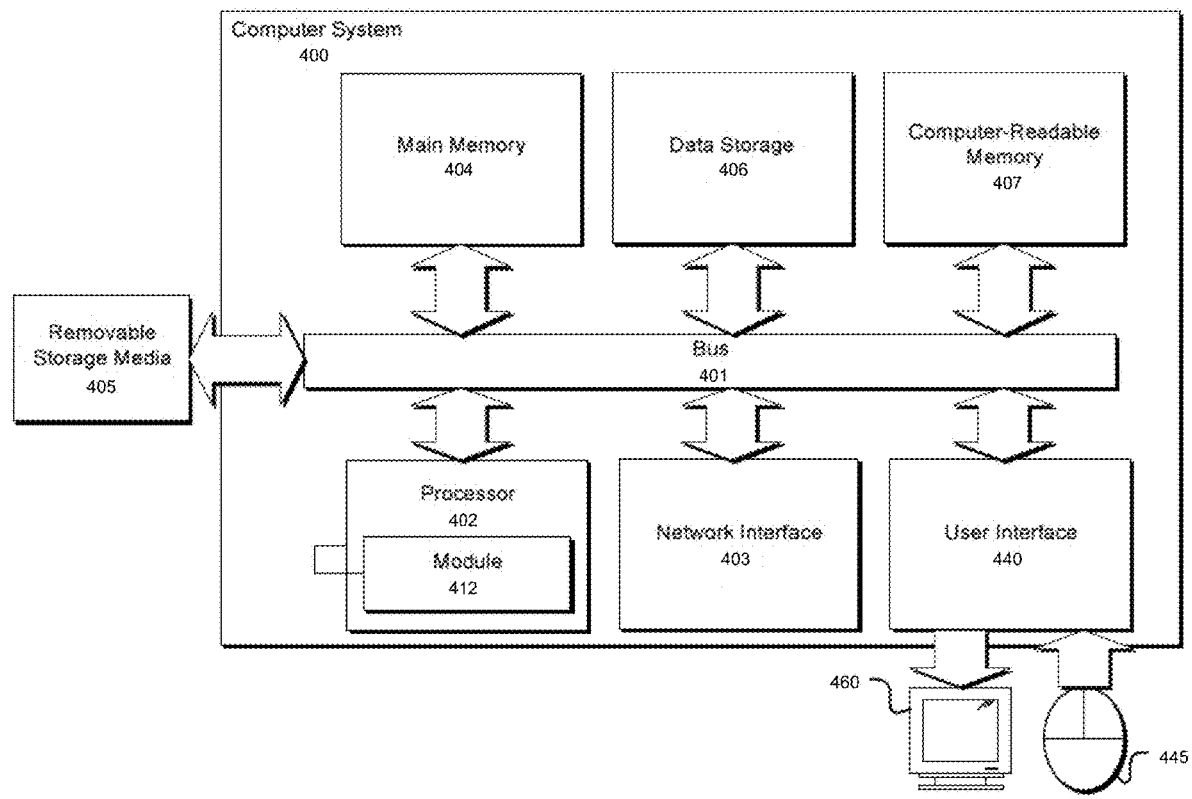
FIG. 10 is an exemplary computing system for use with the system of FIG. 1.

FIG. 10 illustrates an example of a suitable computing system 400 used to implement various aspects of the present system and methods for a research infrastructure for crowdsourcing resources for real time mobile crowd sensing. Example embodiments described herein may be implemented at least in part in electronic circuitry; in computer hardware executing firmware and/or software instructions; and/or in combinations thereof. Example embodiments also may be implemented using a computer program product (e.g., a computer program tangibly or non-transitorily embodied in a machine-readable medium and including instructions for execution by, or to control the operation of, a data processing apparatus, such as, for example, one or more programmable processors or computers). A computer program may be written in any form of programming language, including compiled or interpreted languages, and may be deployed in any form, including as a stand-alone program or as a subroutine or other unit suitable for use in a computing environment. Also, a computer program can be deployed to be executed on one computer, or to be executed on multiple computers at one site or distributed across multiple sites and interconnected by a communication network.

Certain embodiments are described herein as including one or more modules 412. Such modules 412 are hardware-implemented, and thus include at least one tangible unit capable of performing certain operations and may be configured or arranged in a certain manner. For example, a hardware-implemented module 412 may comprise dedicated circuitry that is permanently configured (e.g., as a special-purpose processor, such as a field-programmable gate array (FPGA) or an application-specific integrated circuit (ASIC)) to perform certain operations. A hardware-implemented module 412 may also comprise programmable circuitry (e.g., as encompassed within a general-purpose processor or other programmable processor) that is temporarily configured by software or firmware to perform certain operations. In some example embodiments, one or more computer systems (e.g., a standalone system, a client and/or server computer system, or a peer-to-peer computer system) or one or more processors may be configured by software (e.g., an application or application portion) as a hardware-implemented module 412 that operates to perform certain operations as described herein.

Accordingly, the term "hardware-implemented module" encompasses a tangible entity, be that an entity that is physically constructed, permanently configured (e.g., hardwired), or temporarily configured (e.g., programmed) to operate in a certain manner and/or to perform certain operations described herein. Considering embodiments in which hardware-implemented modules 412 are temporarily configured (e.g., programmed), each of the hardware-implemented modules 412 need not be configured or instantiated at any one instance in time. For example, where the hardware-implemented modules 412 comprise a general-purpose processor configured using software, the general-purpose processor may be configured as respective different hardware-implemented modules 412 at different times. Software may accordingly configure a processor 402, for example, to constitute a particular hardware-implemented module at one instance of time and to constitute a different hardware-implemented module 412 at a different instance of time.

Hardware-implemented modules 412 may provide information to, and/or receive information from, other hardware-implemented modules 412. Accordingly, the described hardware-implemented modules 412 may be regarded as being communicatively coupled. Where multiple of such hardware-implemented modules 412 exist contemporaneously, communications may be achieved through signal transmission (e.g., over appropriate circuits and buses) that connect the hardware-implemented modules. In embodiments in which multiple hardware-implemented modules 412 are configured or instantiated at different times, communications between such hardware-implemented modules may be achieved, for example, through the storage and retrieval of information in memory structures to which the multiple hardware-implemented modules 412 have access. For example, one hardware-implemented module 412 may perform an operation, and may store the output of that operation in a memory device to which it is communicatively coupled. A further hardware-implemented module 412 may then, at a later time, access the memory device to retrieve and process the stored output. Hardware-implemented modules 412 may also initiate communications with input or output devices.

As illustrated, the computing system 400 may be a general purpose computing device, although it is contemplated that the computing system 400 may include other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the general purpose computing device may include various hardware components, such as a processor 402, a main memory 404 (e.g., a system memory), and a system bus 401 that couples various system components of the general purpose computing device to the processor 402. The system bus 401 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computing system 400 may further include a variety of computer-readable media 407 that includes removable/non-removable media and volatile/nonvolatile media, but excludes transitory propagated signals. Computer-readable media 407 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the general purpose computing device. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The main memory 404 includes computer storage media in the form of volatile/nonvolatile memory such as read only memory (ROM) and random access memory (RAM). A basic input/output system (BIOS), containing the basic routines that help to transfer information between elements within the general purpose computing device (e.g., during start-up) is typically stored in ROM. RAM typically contains data and/or program modules that are immediately accessible to and/or presently being operated on by processor 402. For example, in one embodiment, data storage 406 holds an operating system, application programs, and other program modules and program data.

Data storage 406 may also include other removable/non-removable, volatile/nonvolatile computer storage media. For example, data storage 406 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media provide storage of computer-readable instructions, data structures, program modules and other data for the general purpose computing device 400.

A user may enter commands and information through a user interface 440 or other input devices 445 such as a tablet, electronic digitizer, a microphone, keyboard, and/or pointing device, commonly referred to as mouse, trackball or touch pad. Other input devices 445 may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices 445 are often connected to the processor 402 through a user interface 440 that is coupled to the system bus 401, but may be connected by other interface and bus structures, such as a parallel port, game port or a universal serial bus (USB). A monitor 460 or other type of display device is also connected to the system bus 401 via user interface 440, such as a video interface. The monitor 460 may also be integrated with a touch-screen panel or the like.

The general purpose computing device 400 may operate in a networked or cloud-computing environment using logical connections of a network interface 403 to one or more remote devices, such as a remote computer. The remote computer may be a personal computer, a server, a router, a network PC, a peer device or other common network node, and typically includes many or all of the elements described above relative to the general purpose computing device. The logical connection may include one or more local area networks (LAN) and one or more wide area networks (WAN), but may also include other networks. Such networking environments are commonplace in offices, enterprise-wide computer networks, intranets and the Internet.

When used in a networked or cloud-computing environment, the general purpose computing device may be connected to a public and/or private network through the network interface 403. In such embodiments, a modem or other means for establishing communications over the network is connected to the system bus 401 via the network interface 403 or other appropriate mechanism. A wireless networking component including an interface and antenna may be coupled through a suitable device such as an access point or peer computer to a network. In a networked environment, program modules depicted relative to the general purpose computing device, or portions thereof, may be stored in the remote memory storage device.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method, comprising:
    determining context requirements including requirements for a plurality of device attributes of each volunteer device of a plurality of volunteer devices, wherein the context requirements are representative of device attributes and/or available resources needed for execution of a mobile crowd sensing task, wherein the determining context attributes further includes:
        determining a difference value between a context value and a context requirement value for a particular device attribute for a volunteer device of the plurality of volunteer devices;
        normalizing the difference value relative to other attributes to produce a context matching index for each device attribute;
        obtaining a context sense index for each volunteer device of the plurality of volunteer devices, wherein the context sense index is a weighted sum of each difference value for each device attribute;
        determining a penalty value for each volunteer device of the plurality of volunteer devices based on the respective context sense index, and
        minimizing an objective function such that a set of selected devices is selected which minimize the penalty value and minimize a time varying operational overhead while maintaining a minimum standard of resource availability;
    obtaining context capability information including device attributes and/or available resources from each volunteer device of the plurality of volunteer devices;
    evaluating the context capability information for each volunteer device of the plurality of volunteer devices relative to the context requirements for each device attribute, wherein a deviation of context capability information from the context requirements is associated with a penalty; and
    selecting an optimal set of selected devices from the plurality of volunteer devices that best meet the context requirements by minimizing the associated penalty while maintaining a minimum standard of resource availability.

2. The method of claim 1, wherein the step of evaluating context attributes is executed using expected context values, wherein the expected context values are determined using one or more stochastic models.

3. The method of claim 2, wherein the expected context value for each device attribute for a particular volunteer device of the plurality of volunteer devices is determined by examining historical context value trends.

4. The method of claim 1, wherein the step of evaluating context attributes is executed using current context values, wherein the current context values are empirically determined.

5. The method of claim 1, wherein the penalty value for a volunteer device of the plurality of volunteer devices is given the value of the context sense index for that particular volunteer of the plurality of volunteer devices if the difference values are within an acceptable range and wherein the penalty value for the particular volunteer device of the plurality of volunteer devices is given a large value if the difference values are not within an acceptable range.

6. The method of claim 1, wherein the objective function requires that a total time varying operational overhead value is less than an execution time constraint value, wherein the time varying operational overhead includes time taken for data sensing and data transfer time.

7. The method of claim 1, wherein the objective function requires that a difference between resource availability and resource usage for a volunteer device of the plurality of volunteer devices is greater than a minimum resource limit value.

* * * * *